United States Patent [19]

Tajima et al.

[11] Patent Number: 4,822,522
[45] Date of Patent: Apr. 18, 1989

[54] HINDERED PHENOL AMIDES

[75] Inventors: Kenji Tajima, Kuwana; Takao Nishina, Kitamoto; Kazunori Nishikawa, Matsudo, all of Japan

[73] Assignee: Adeka Argus Chemical Co., Ltd., Urawa, Japan

[21] Appl. No.: 89,463

[22] Filed: Aug. 26, 1987

Related U.S. Application Data

[63] Continuation-in-part of Ser. No. 18,878, Feb. 25, 1987, abandoned.

[30] Foreign Application Priority Data

Feb. 26, 1986 [JP] Japan .................. 61-41107

[51] Int. Cl.$^4$ .......... C09K 15/32; C08K 5/15; C07D 319/08
[52] U.S. Cl. .................. 252/400.24; 549/335; 524/108; 252/400.52; 252/400.53; 252/400.61
[58] Field of Search .......... 549/335; 524/108; 252/400.24, 400.52, 400.53, 400.61

[56] References Cited

FOREIGN PATENT DOCUMENTS 62-63590 3/1987 Japan .................. 549/335

Primary Examiner—Nicky Chan

[57] ABSTRACT

Hindered phenol amides are provided having the following formula:

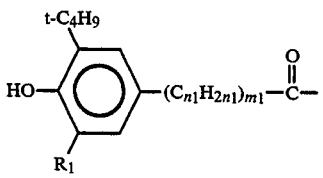

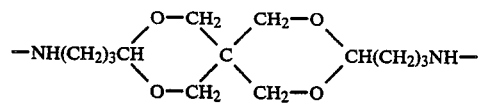

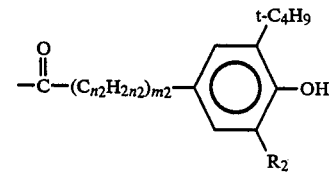

wherein:
R$_1$ and R$_2$ are hydrogen or lower alkyl having from one to four carbon atoms;
m$_1$ and m$_2$ are 0 or 1; and
n$_1$ and n$_2$ are selected from 1, 2 and 3; as well as stabilizer compositions for synthetic polymers and synthetic polymer compositions containing such hindered phenol amides.

21 Claims, No Drawings

HINDERED PHENOL AMIDES

This application is a continuation-in-part of Ser. No. 18,878, filed Feb. 25, 1987.

Hindered phenols are known antioxidants for organic materials, especially for synthetic resins. However, hindered phenols have a relatively low molecular weight, and therefore an insufficient stabilizing effect. Accordingly, hydroxyphenylcarboxylic acid esters and amides of higher molecular weight have been proposed as antioxidants.

For example, hydroxyphenylcarboxylic acid amides of aliphatic amines are disclosed in Japanese Pat. No. 16483/81. However, the stabilizing effect of these compounds is not satisfactory.

In accordance with this invention, hindered phenol amides having an excellent stabilizing effect are provided, having the formula:

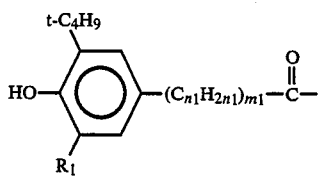

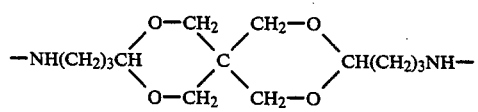

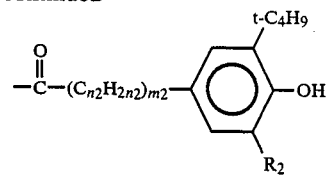

wherein:

$R_1$ and $R_2$ are hydrogen or lower alkyl having from one to four carbon atoms;

$m_1$ and $m_2$ are 0 or 1; and $n_1$ and $n_2$ are selected from 1, 2 and 3.

$R_1$ and $R_2$, $m_1$ and $m_2$ and $n_1$ and $n_2$ can be the same or different.

Exemplary $R_1$ and $R_2$ lower alkyl include methyl, ethyl, propyl, isopropyl, butyl, isobutyl, sec-butyl and tert-butyl.

These hindered phenols of Formula I can be readily prepared by the reaction of a hydroxyphenylcarboxylic acid of Formula II or mixture thereof as well as derivatives thereof, for example, the corresponding lower alkyl ester, phenyl ester or acid halide, with 3,9-bis(3'-aminopropyl)-2,4,8,10-tetraoxaspiro[5.5]undecane (ATU).

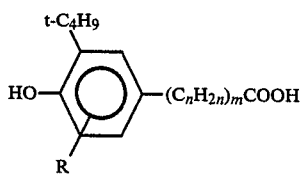

II where R is $R_1$ or $R_2$, n is $n_1$ or $n_2$, and m is $m_1$ or $m_2$.

The following hindered phenol amides of the invention are exemplary:

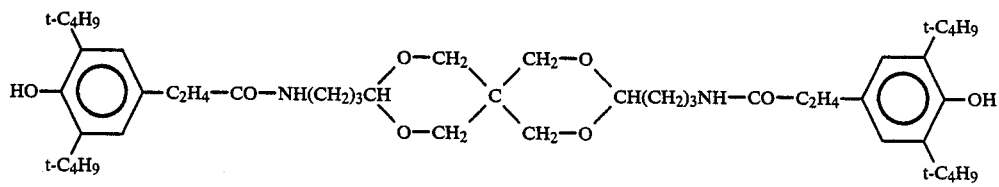

1.

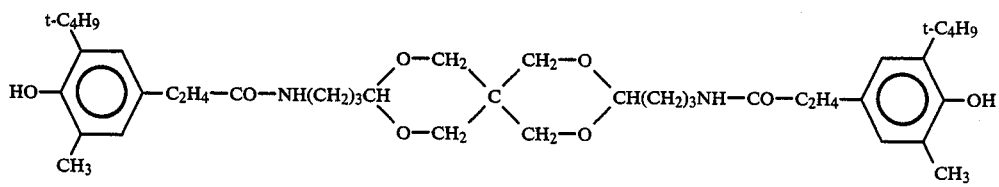

2.

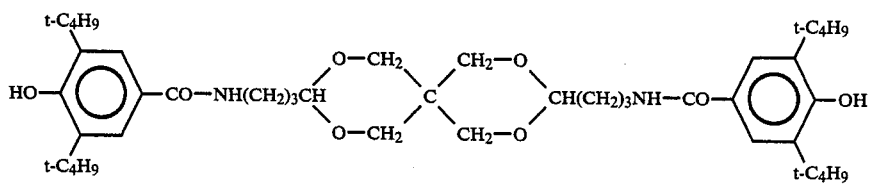

3.

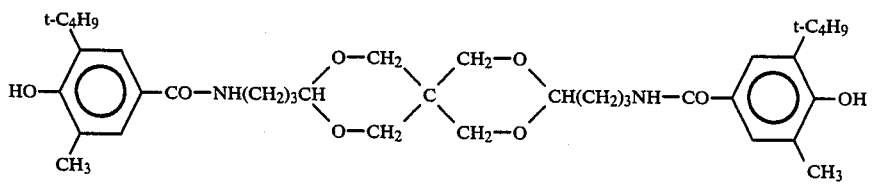

4.

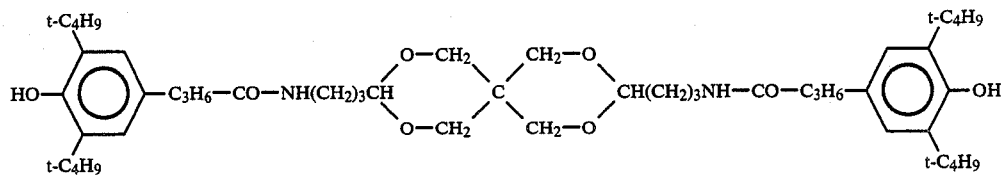
5.
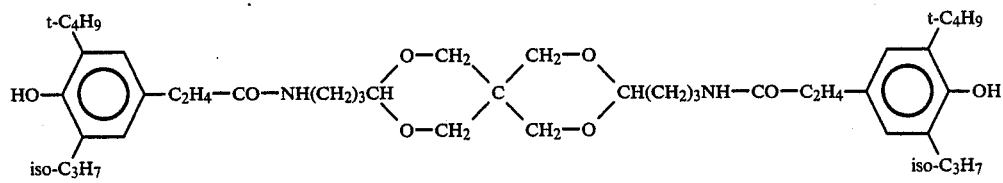
6.
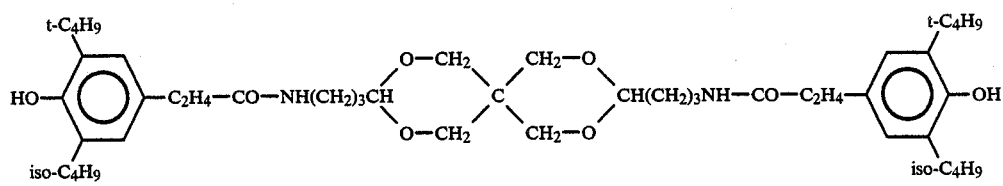
7.
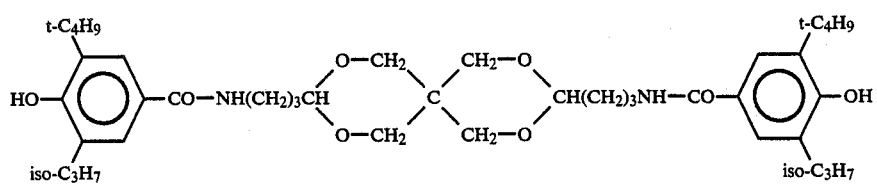
8.
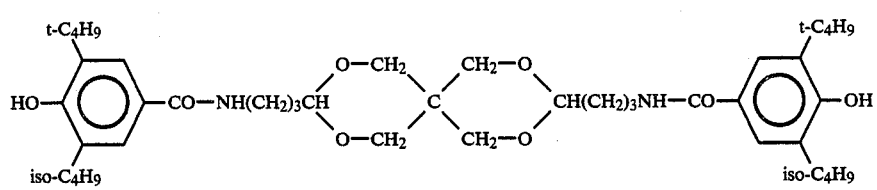
9.
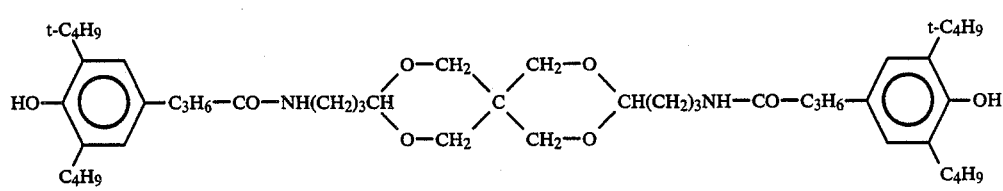
10.
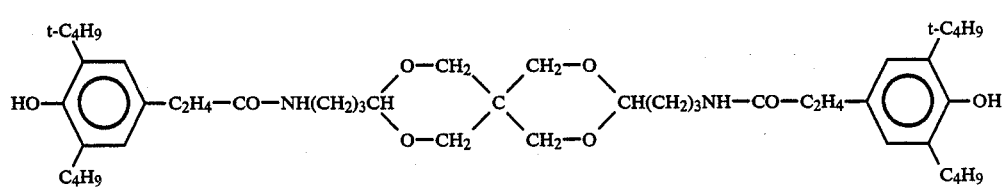
11.
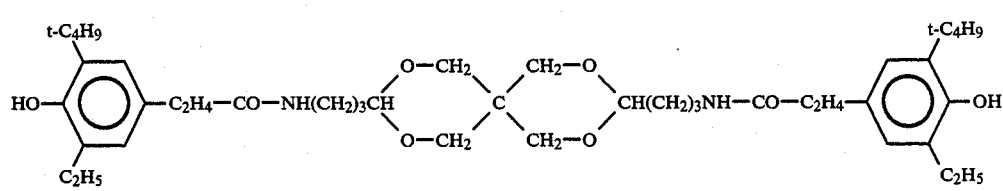
12.
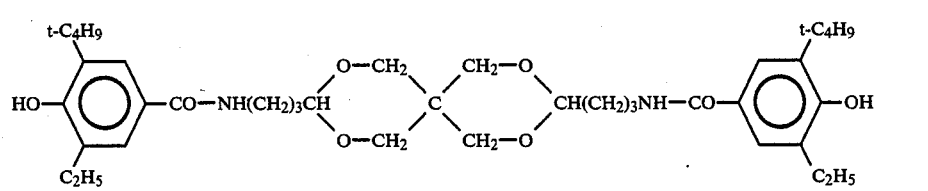
13.

-continued
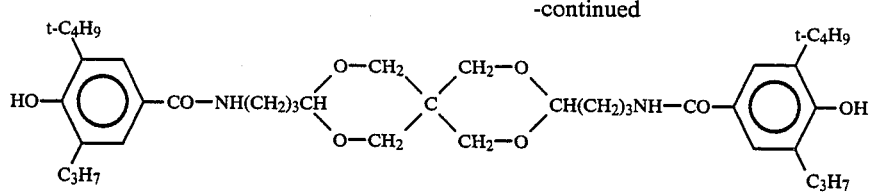 14.
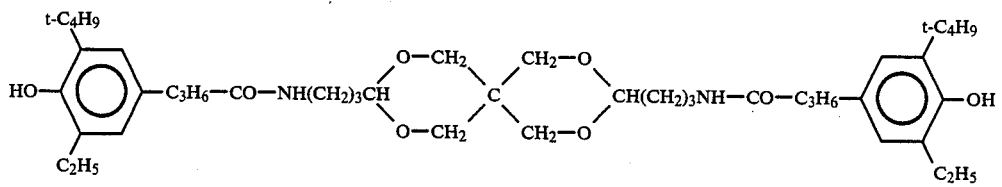 15.
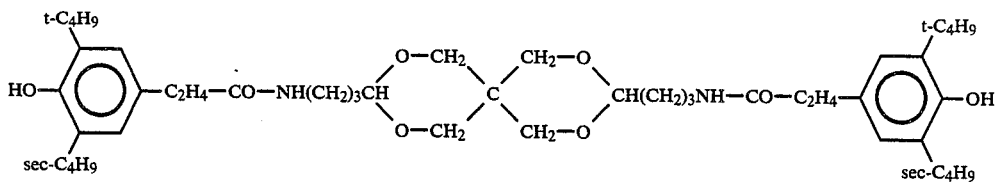 16.
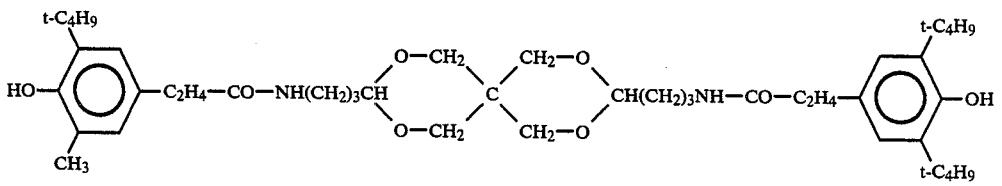 17.
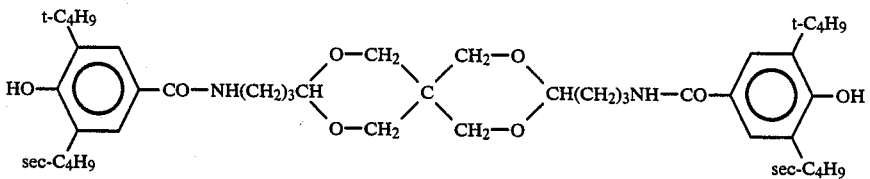 18.
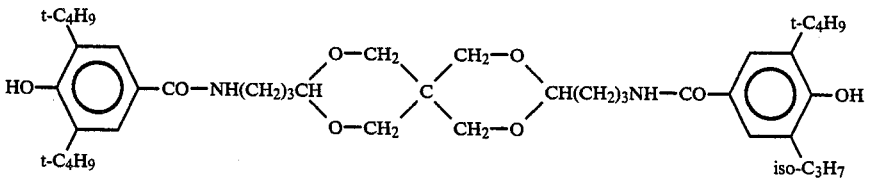 19.
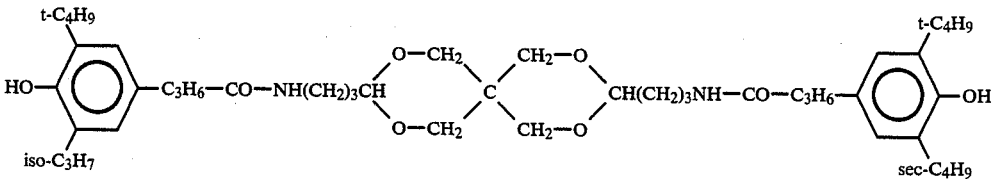 20.
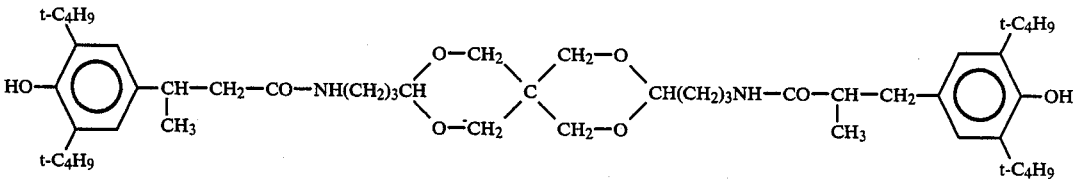 21.
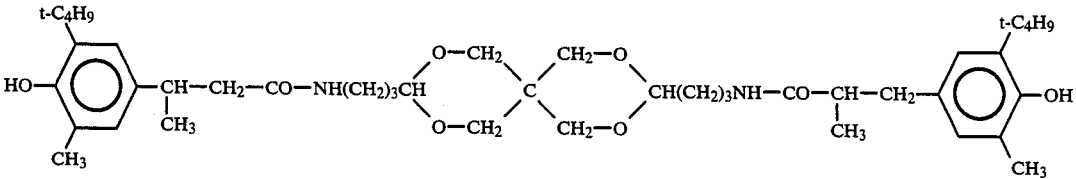 22.

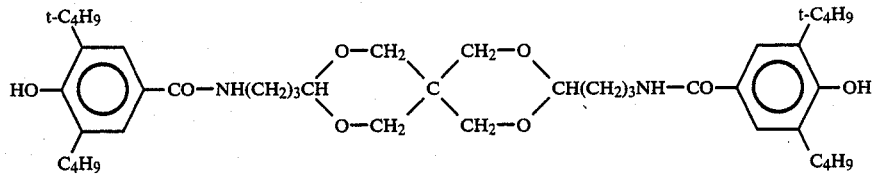

23.

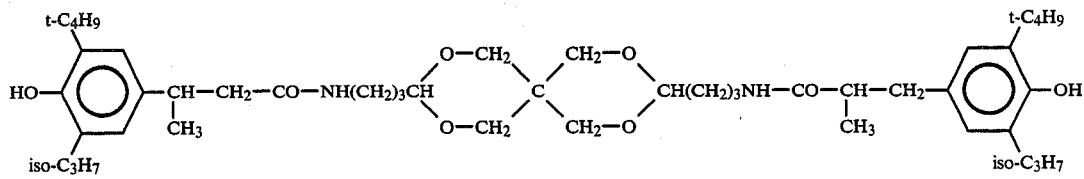

24.

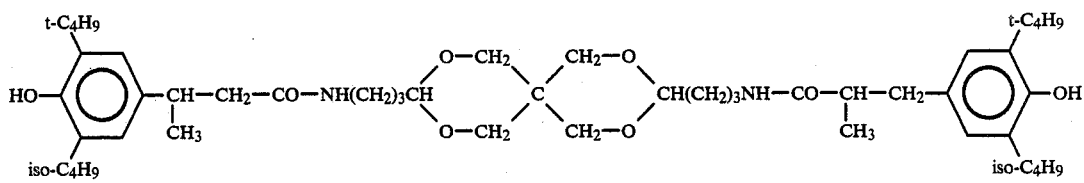

25.

The following Examples represent preferred embodiments of the preparation of preferred hindered phenol amides of the invention:

EXAMPLE I

Preparation of 3,9-bis(3'-aminopropyl)-2,4,8,10-tetraoxaspiro[5.5]undecane-bis(3,5-di-t-butyl-4-hydroxyphenylpropionic acid amide)

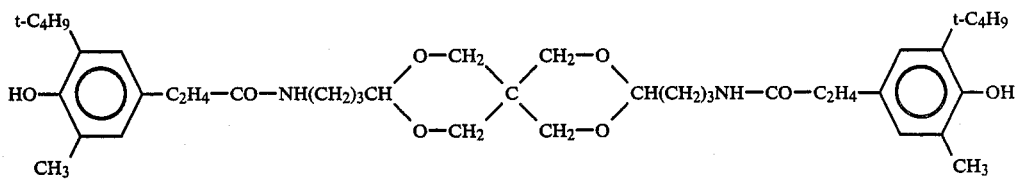

Methyl-3,5-di-t-butyl-4-hydroxyphenylpropionate 306.6 g (1.05 mol), (3,9-bis(3'-aminopropyl)-2,4,8,10-tetraoxaspiro[5.5]undecane) 137 g (0.5 mol) and 44.3 g of mineral spirits were stirred at 160° C. for one hour under a stream of nitrogen. The reaction mixture was then stirred for an additional 3 hours at 160° C. under 200 mm Hg.

Excess methyl ester and the solvent were distilled off at 160° C./5 mmHg, and a pale yellow solid, melting at 71° C., was obtained.

Infrared analysis: 3600 and 3650 cm$^{-1}$: phenol, 2960 and 1440 cm$^{-1}$: alkyl, 770 and 720 cm$^{-1}$: benzene ring, 1640 and 1540 cm$^{-1}$: amide, 3550 cm$^{-1}$: NH, 1210 and 1160 cm$^{-1}$: ether

EXAMPLE II

Preparation of 3,9-bis(3'-aminopropyl)-2,4,8,10-tetraoxaspiro[5.5]undecane-bis(3-t-butyl-4-hydroxy-5-methylphenylpropionic acid amide)

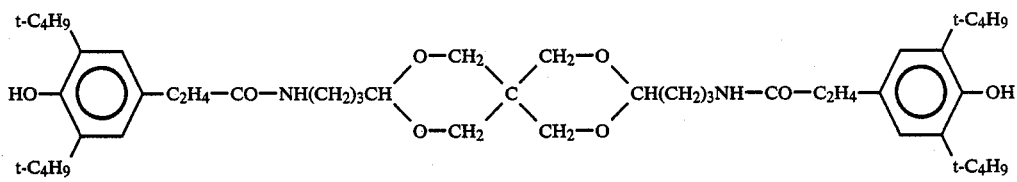

The procedure of Example I was repeated, employing methyl-3-t-butyl-4-hydroxy-5-methylphenylpropionate 306.6 g (1.05 mol) instead of methyl-3,5-di-t-butyl-4-hydroxyphenylpropionate. A pale yellow solid melting at 71° C. was obtained.

Infrared analysis: 3400 cm$^{-1}$: phenol, 2960 and 1440 cm$^{-1}$: alkyl, 770 and 720 cm$^{-1}$: benzene ring, 1640 and 1540 cm$^{-1}$: amide, 3350 cm$^{-1}$: NH, 1210 and 1160 cm$^{-1}$: ether

EXAMPLES III TO V

The following compounds were prepared using the procedure of Example I:

III 3,9-bis(3'-aminopropyl)-2,4,8,10-tetraoxaspiro[5.5]undecane-bis(3,5-di-t-butyl-4-hydroxybenzoic acid amide)

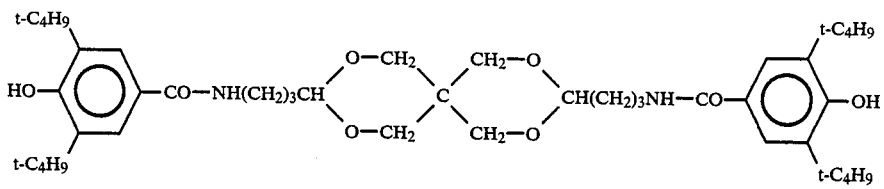

IV 3,9-bis(3'-aminopropyl)-2,4,8,10-tetraoxaspiro[5.5]undecane-bis(3-t-butyl-4-hydroxy-5-methylbenzoic acid amide)

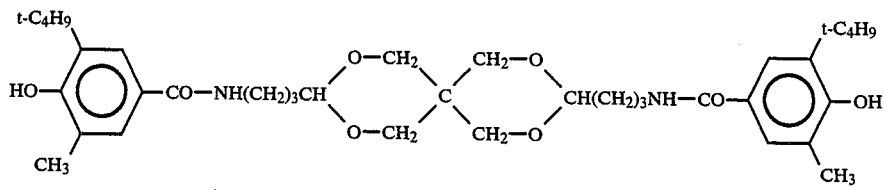

V 3,9-bis(3'-aminopropyl)-2,4,8,10-tetraoxaspiro[5.5]undecane-bis(3,5-di-t-butyl-4-hydroxybutylic acid amide)

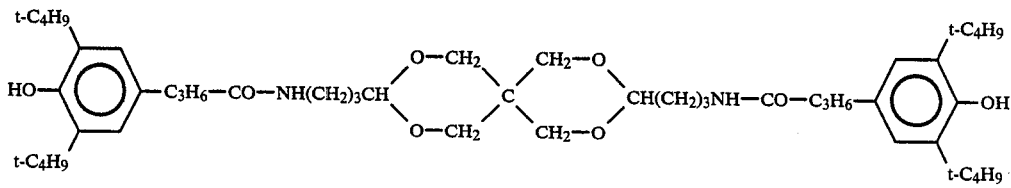

The hindered phenol amides of this invention are effective antioxidants and heat stabilizers for organic substrates, particulaly saturated and unsaturated aliphatic, cycloaliphatic and aromatic hydrocarbons, synthetic and natural oils and fats, synthetic ester oil, petroleum oils and lubricants, and synthetic polymeric materials, that are subject to deterioration when exposed to oxygen, heat and/or light. Small amounts are effective. An amount within the range from about 0.001 to about 5 parts, preferably from 0.01 to 3 parts, by weight per 100 parts by weight of the substrate polymer is usually sufficient. Larger amounts can be used, if desired.

Synthetic polymers that can have their resistance to deterioration enhanced with the hindered phenol amides according to this invention include α-olefin polymers such as polyethylene, polypropylene, polybutene, poly-3-methylbutene, poly-3-methyl pentene, and mixtures thereof, and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, such as polyethyleneterephthalate and polybutyleneterephthalate; polyphenyleneoxide; polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, polyvinylbromide, polyvinylfluoride, polyvinylidenechloride, chlorinated polyethylene, chlorinated polypropylene, chlorinated rubber, and copolymers thereof, vinylchloride/vinylacetate copolymer, vinylchloride/ethylene copolymer, vinylchloride/propylene copolymer, vinylchloride/styrene copolymer, vinylchloride/styrene/maleic anhydride terpolymer, vinylchloride/butadiene copolymer, vinylchloride/acrylic acid ester copolymer, vinylchloride/methacrylic acid copolymer, vinylchloride/acrylonitrile copolymer; and rubbers such as isoprene rubber, butadiene rubber, epichlorohydrin rubber, chloroprene rubber, and blends of any of the above.

The hindered phenol amides of the invention can be combined with conventional heat stabilizers such as other phenolic antioxidants, polyvalent metal salts of organic acids, organic phosphites, thioethers, and other known heat stabilizers, thereby constituting stabilizer compositions of the invention.

When the stablizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted fuoric acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

$$R_1-O-P-O-R_3$$
$$|$$
$$O$$
$$|$$
$$R_2$$

in which
$R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

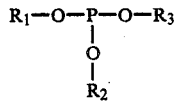

in which
$R_4$ is a bivalent organic radical selected from the group consisting of alkylene, arylene, aralkylene, alkarylene and cycloalkylene radicals having from two to about thirty carbon atoms, and $R_6$ is a monovalent organic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

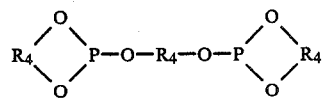

More complex triphosphites are formed from trivalent organic radicals, of the type:

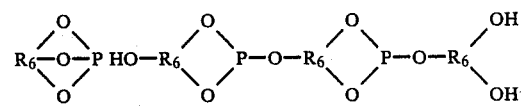

in which
$R_6$ is a trivalent organic radical of any of the types of $R_1$ to $R_5$, inclusive, as defined above.

A particularly useful class of complex triphosphites are the tetraoxadiphosphaspiro undecanes of the formula:

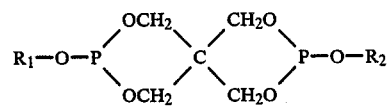

where
$R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites having a bicyclic aromatic group attached to phosphorus through oxygen, with no or one or more phenolic hydroxyl groups on either or both of the aromatic rings. These phosphites are characterized by the formula:

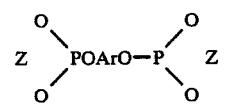

or

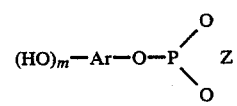

in which
Ar is a mono or bicyclic aromatic nucleus and m is an integer of from 0 to about 5. $Z$ is one or a plurality of organic radicals as defined above for $R_1$ to $R_6$, taken singly or together in sufficient number to satisfy the valences of the two phosphite oxygen atoms.

One or both $Z$ radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(-phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy) ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites ae: bis(4,4'-thio-bis(2-tertiary-butyl-5-methyl-phenol))isooctyl phosphite, mono(4,4'-thio-bis(2-tertiary-butyl-5-methyl-phenol))di-phenyl phosphite, tri-(4,4'-n-butylidene-bis(2-tertiary-butyl-5-methylphenol))phosphite, (4,4'-benzylidene-bis(2-tertiary-butyl-5-methyl-phenol)-)diphenyl phosphite, isooctyl 2,2'-bis(parahydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bis-phenyl polyphosphite, 2-ethylhexyl-2,2'-methylene-bis(4-methyl-6,1'-methyl-cyclohexyl)phenyl triphosphite, tertra-tridecyl-4,4'-oxydiphenyl diphosphite, tetra-n-dodecyl-4,4'-n-butylidene bis(2-tertiarybutyl)-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, decresyl phosphite, di-(o-isooctylphenyl)phosphite, di(p-ethylhexylphenyl)phosphite, di(p-t-octylphenyl)-phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenylphosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))-phosphite, (4,4'-thio-bis(2-tertiary-butyl-5-methyl-phenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenol))phosphite, mono-2-ethylhexyl-mono-2,2'-methylene-bis(4-methyl-6,1'-methyl-cyclohexyl)phenol phosphite, bis(2,2'-bis(para-hydroxyphenyl)propane)phosphite, monoisooctylmono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-decyl-4,4'-n-butylidene-bis(2-tertiary-butyl-5-methylphenyl)diphosphite, triisooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

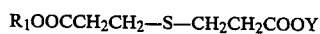

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

—XO[OCCH$_2$CH$_2$SCH$_2$CH$_2$COOXO]$_n$OCCH$_2$CH$_2$—S—CH$_2$CH$_2$ COOZ where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylenearylene and mixed alkylene-cycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
 (a) $R_1OOCCH_2CH_2SCH_2CH_2COOH$
 (b) $R_1OOCCH_2CH_2SCH_2CH_2COOR_2$
 (c) $R_1O[OCCH_2CH_2SCH_2CH_2COOX-O]_{n}OCCH_2CH_2SCH_2CH_2COOZ$
 (d) $R_1OOCCH_2CH_2SCH_2CH_2COOM$ In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility with nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as

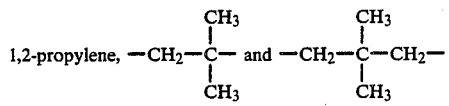

arylene radicals such as

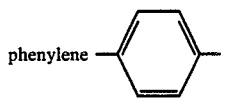

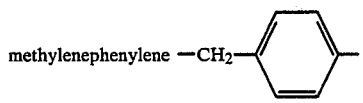

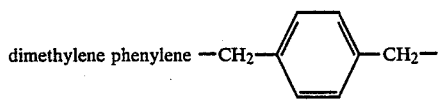

and alicyclylene such as

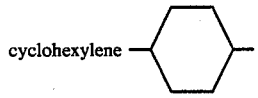

and

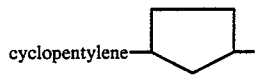

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodiopropionate, monooleyl thiodipropionic acid, hydroxyethyl lauryl thiodipropionate monoglycerol thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:
(1) Thioalkunoic acid amides of Tokuno et al Japanese Pat. No. 16,286/68 having the formula:

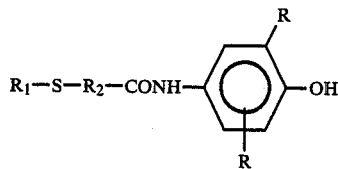

R is alkyl of one to eight carbon atoms, $R_1$ is allyl of six to twenty-four carbon atoms, and $R_2$ is alkylene of one to six carbon atoms.

(2) Thioalkanoic acid amides of 1,3,5-triazines of Ozeki et al Japanese Pat. No. 20,366/68 having the formula:

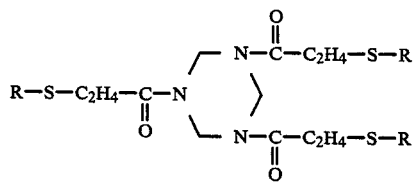

R is alkyl of eight to eighteen carbon atoms.

(3) Bis-thioalkanoic acid amides of Yamamoto et al Japanese Pat. No. 23,765/68 having the formula:

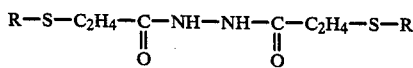

R is alkyl of more than six carbon atoms, aryl or aralkyl.

(4) Bis-thioalkylanoic acid amides of Ozeki et al Japanese Pat. No. 26,184/69 having the formula:

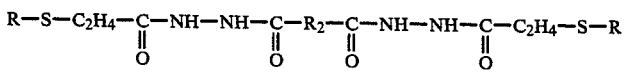

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

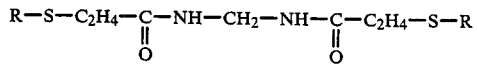

R is alkyl of more than six carbon atoms, aryl, or aralkyl.

(6) Thioalkanoic acid amide derivatives of Minagawa et al, published Japanese application No. 106,484/74 having the formula:

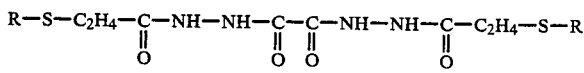

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

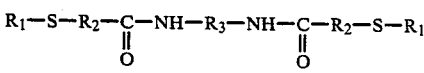

wherein:
$R_1$ is alkyl having from one to about fifty carbon atoms;
$R_2$ is alkylene having from one to about three carbon atoms; and
$R_3$ is alkylene having from about two to about twelve carbon atoms.

$\beta$-Alkylthiopropionic acid esters having the general formula:

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl) 5-chlorobenzotriazole, 2(2-hydroxy-3,5-di-t-amylphenyl)-benzotriazole, benzoates such as phenylsalicylate, 2,4-di-t-butylphenyl-3,5-di-t-butyl-4-hydroxy phenylbenzoate, nickel compound such as nickel-2,2'-thiobis(4-t-octyl-phenolate), nickel-monoethyl(3,5-di-t-butyl-4-hyroxybenzyl)phosphonate, substituted acrylonitriles such as methyl-$\alpha$-cyano-$\beta$-methyl-$\beta$-(p-methoxy phenyl) acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or stabilizer composition is used to improve the resistance of the organic substrate, such as the synthetic polymer to deterioration in physical properties when exposed to oxygen, heat and/or light, including, for example, discoloration, reduction in melt viscosity and embrittlement. Very small amounts are usually adequate. Amounts within the range from about 0.001 to about 10% total stabilizers (including the hindered phenol amide of the invention) by weight of the substrate (polymer) are satisfactory. Preferably, from 0.01 to 5% is employed, for optimum stabilization.

The stabilizer compositions of the invention are readily rendered in solid particulate form, comprising a blend of:

(a) hindered phenol amide in an amount of from about 10 to about 35 parts by weight;

(b) another heat stabilizer or stabilizers in an amount from about 10 to about 35 parts by weight;

and optionally:

(c) a light stabilizer or stabilizers in an amount of from about 10 to about 35 parts by weight.

The hindered phenol amide stabilizer of the invention can be employed in combination with conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; epoxy compounds; and organic phosphites.

With polyolefin resins there can be employed fatty acid salts of polyvalent metals, organic phosphites, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or composition is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then rmoved from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples represent preferred embodiments of synthetic polymer compositions containing the stabilizers in accordance with the invention.

EXAMPLES 1 TO 5

Polypropylene compositions were prepared using stabilizers of the invention and of the prior art, and having the following formulation:

| Ingredient | Parts by Weight |
| --- | --- |
| Polypropylene | 100 |
| Calcium stearate | 0.2 |
| Stabilizer as shown in Table I | 0.2 |

The compositions were thoroughly blended in a mixer, and then extruded at 240° C. to prepare pellets. Test pieces 1 mm thick were then molded by injection molding at 250° C.

The test pieces were heated at 160° C. in a Geer oven, and the hours to failure were noted. The yellowness index of the pieces before and after exposure to fluorescent light for 72 hours at room temperature was also noted.

The results are shown in Table I.

TABLE I
| Example | Stabilizer | Hours to Failure | Yellowness Index Original | Yellowness Index After 72 hours |
|---|---|---|---|---|
| Control | Hexamethylenebis(3,5-di-t-butyl-4-hydroxyphenyl)propionic acid amide | 260 | 11.2 | 14.3 |
| Example 1 | 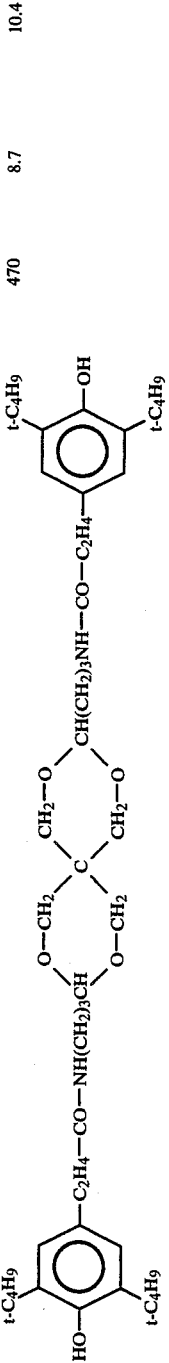 | 470 | 8.7 | 10.4 |
| Example 2 | 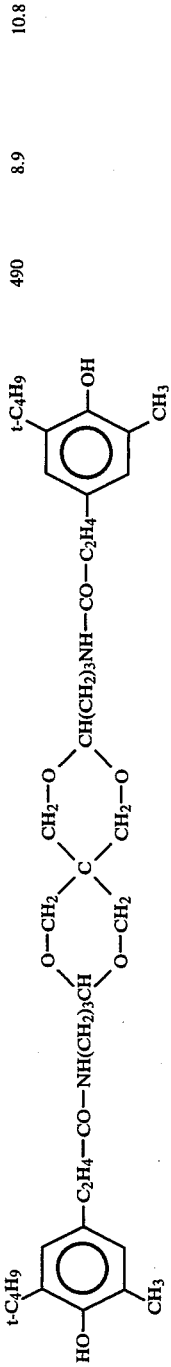 | 490 | 8.9 | 10.8 |
| Example 3 | 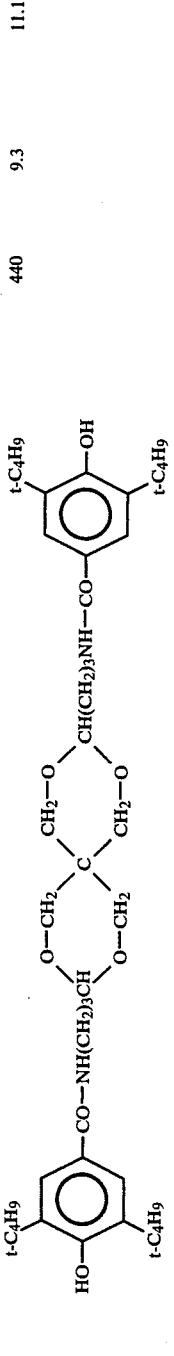 | 440 | 9.3 | 11.1 |
| Example 4 | 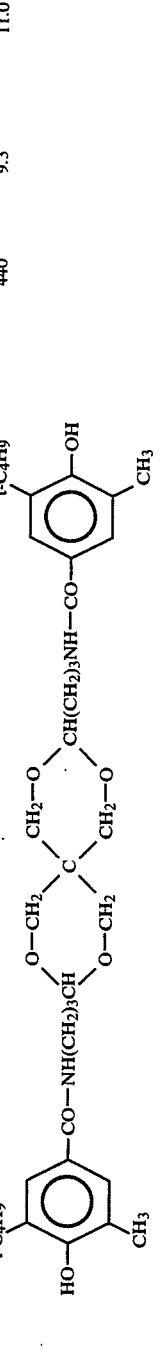 | 440 | 9.3 | 11.0 |
| Example 5 | 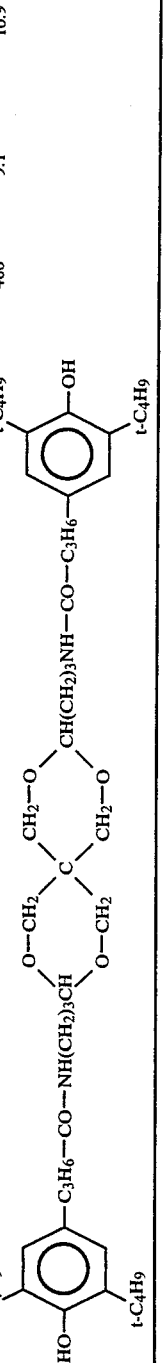 | 460 | 9.1 | 10.9 |

The superiority in effectiveness of the hindered phenol amides of the invention to the hindered phenol of the prior art is evident from the data, in terms both of duration and color.

EXAMPLES 6 TO 10

Nylon 12 (polymer of 12-amine dodecanoic acid) compositions were prepared using stabilizers of the invention and of the prior art, and having the following formulation:

| Ingredient | Parts by Weight |
|---|---|
| Unstabilized Nylon 12 | 100 |
| Stabilizer as shown in Table II | 0.5 |

The compositions were thoroughly blended in a mixer, and then extruded at 240° C. to prepare pellets. Test pieces 1.5 mm thick were then molded by injection molding at 280° C.

The test pieces were heated at 160° C. in a Geer oven, and stress-strain tests were carried out. The days to failure were determined as the days when the yield stress of the test pieces was lowered at 80% of that of unaged pieces.

The results are shown in Table II.

1. Hindered phenol amides having the formula:

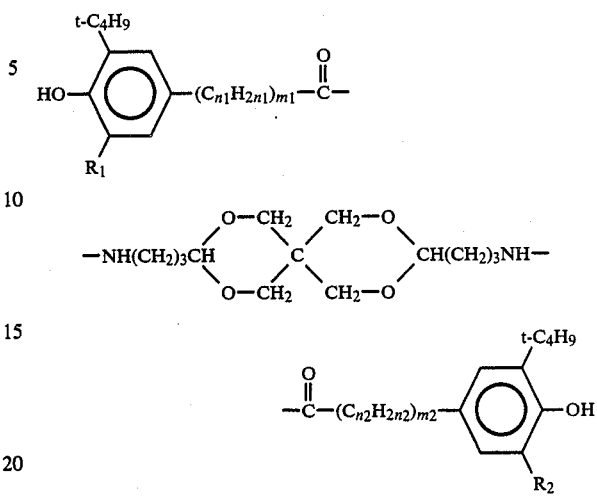

wherein:

$R_1$ and $R_2$ are hydrogen or lower alkyl having from one to four carbon atoms;

$m_1$ and $m_2$ are 0 or 1; and

TABLE II

| Example | Stabilizer | Days to Failure |
|---|---|---|
| Control 1 | None | 5.5 |
| Control 2 | Hexamethylenebis(3,5-di-t-butyl-4-hydroxyphenylpropionic acid amide) | 16.0 |
| Example 6 | HO—[3,5-di-t-C$_4$H$_9$-phenyl]—C$_2$H$_4$—CO—NH(CH$_2$)$_3$CH(O—CH$_2$)$_2$C(CH$_2$—O)$_2$CH(CH$_2$)$_3$NH—CO—C$_2$H$_4$—[3,5-di-t-C$_4$H$_9$-phenyl]—OH | 21.0 |
| Example 7 | HO—[3-t-C$_4$H$_9$-5-CH$_3$-phenyl]—C$_2$H$_4$—CO—NH(CH$_2$)$_3$CH(O—CH$_2$)$_2$C(CH$_2$—O)$_2$CH(CH$_2$)$_3$NH—CO—C$_2$H$_4$—[3-t-C$_4$H$_9$-5-CH$_3$-phenyl]—OH | 20.5 |
| Example 8 | HO—[3,5-di-t-C$_4$H$_9$-phenyl]—CO—NH(CH$_2$)$_3$CH(O—CH$_2$)$_2$C(CH$_2$—O)$_2$CH(CH$_2$)$_3$NH—CO—[3,5-di-t-C$_4$H$_9$-phenyl]—OH | 18.5 |
| Example 9 | HO—[3-t-C$_4$H$_9$-5-CH$_3$-phenyl]—CO—NH(CH$_2$)$_3$CH(O—CH$_2$)$_2$C(CH$_2$—O)$_2$CH(CH$_2$)$_3$NH—CO—[3-t-C$_4$H$_9$-5-CH$_3$-phenyl]—OH | 18.5 |
| Example 10 | HO—[3,5-di-t-C$_4$H$_9$-phenyl]—C$_3$H$_6$—CO—NH(CH$_2$)$_3$CH(O—CH$_2$)$_2$C(CH$_2$—O)$_2$CH(CH$_2$)$_3$NH—CO—C$_3$H$_6$—[3,5-di-t-C$_4$H$_9$-phenyl]—OH | 19.0 |

The superiority in effectiveness of the hindered phenol amides of the invention to the hindered phenol of the prior art is evident from the data.

Having regard to the foregoing disclosure, the following is claimed is inventive and patentable embodiments thereof:

$n_1$ and $n_2$ are selected from 1, 2 and 3.

2. A compound according to claim 1 in which at least one of $R_1$ and $R_2$ is tert-butyl.

3. A compound according to claim 2 in which both $R_1$ and $R_2$ are tert-butyl.

4. A compound according to claim 1 in which at least one of $R_1$ and $R_2$ is methyl.

5. A compound according to claim 4 in which both $R_1$ and $R_2$ is methyl.

6. A compound according to claim 1 in which $m_1$ and $m_2$ are zero.

7. A compound according to claim 1 in which $m_1$ and $m_2$ are 1.

8. A compound according to claim 1 in which $n_1$ and $n_2$ are 1.

9. A compound according to claim 1 in which $n_1$ and $n_2$ are 2.

10. A compound according to claim 1 in which $n_1$ and $n_2$ are 3.

11. A compound according to claim 1 having the formula:

16. An olefin polymer composition having improved resistance to deterioration upon exposure to light comprising an olefin polymer selected from the group consisting of polymers of alpha-olefins having from two to six carbon atoms and polystyrene, and a compound in accordance with claim 1.

17. An olefin polymer composition in accordance with claim 16 wherein the polyolefin is polypropylene.

18. A polyamide polymer composition having improved resistance to deterioration upon exposure to light comprising a polyamide and a compound in accordance with claim 1.

19. A stabilizer composition for enhancing the resistance of synthetic polymers to deterioration upon exposure to oxygen, heat and/or light, comprising a compound in accordance with claim 1 and at least one syn-

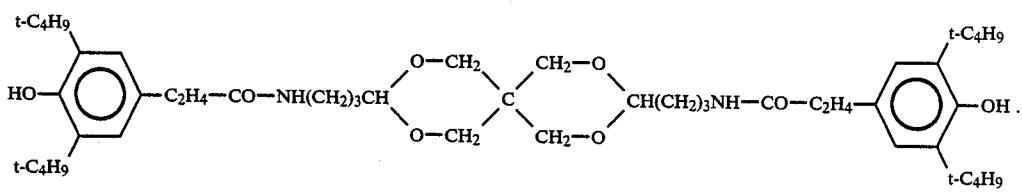

12. A compound according to claim 1 having the formula:

thetic polymer heat stabilizer selected from the group consisting of organic phosphites and polyvalent metal

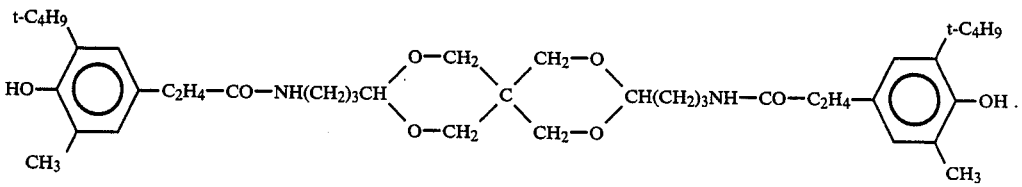

13. A compound according to claim 1 having the formula:

salts.

20. A stabilizer composition according to claim 19, in

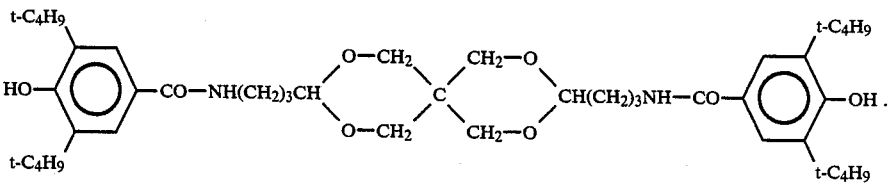

14. A compound according to claim 1 having the formula which the heat stabilizer is an organic phosphite.

21. A stabilizer composition according to claim 19, in

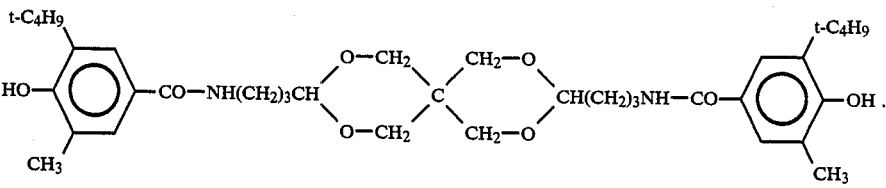

15. A compound according to claim 1 having the formula:

which the heat stabilizer is a polyvalent metal salt.

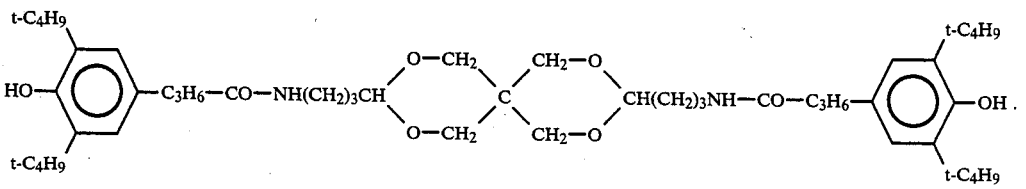

* * * * *